(12) United States Patent
Sugizaki et al.

(10) Patent No.: US 11,874,244 B2
(45) Date of Patent: Jan. 16, 2024

(54) APPARATUS FOR MAINTAINING LIQUID MEMBRANE AND SENSOR APPARATUS

(71) Applicant: KABUSHIKI KAISHA TOSHIBA, Minato-ku (JP)

(72) Inventors: Yoshiaki Sugizaki, Fujisawa (JP); Tatsuro Saito, Kawasaki (JP)

(73) Assignee: KABUSHIKI KAISHA TOSHIBA, Minato-ku (JP)

(*) Notice: Subject to any disclaimer, the term of this patent is extended or adjusted under 35 U.S.C. 154(b) by 443 days.

(21) Appl. No.: 16/818,075

(22) Filed: Mar. 13, 2020

(65) Prior Publication Data

US 2021/0080416 A1 Mar. 18, 2021

(30) Foreign Application Priority Data

Sep. 17, 2019 (JP) .................................. 2019-168663

(51) Int. Cl.
| | | |
|---|---|---|
| G01N 27/12 | (2006.01) | |
| G01N 33/497 | (2006.01) | |
| B01L 3/00 | (2006.01) | |
| G01N 33/543 | (2006.01) | |
| G01N 27/414 | (2006.01) | |
| H01L 29/16 | (2006.01) | |

(52) U.S. Cl.
CPC .............. *G01N 27/12* (2013.01); *B01L 3/508* (2013.01); *G01N 27/4141* (2013.01); *G01N 33/497* (2013.01); *G01N 33/54373* (2013.01); *B01L 2300/06* (2013.01); *B01L 2300/12* (2013.01); *H01L 29/1606* (2013.01)

(58) Field of Classification Search
CPC .... B01L 3/5023; B01L 3/508; B01L 2300/06; B01L 2300/0663; B01L 2300/0825; B01L 2300/12; B01L 2400/0406; G01N 27/12; G01N 27/127; G01N 27/4141; G01N 33/497; G01N 33/54373; H01L 29/1606
See application file for complete search history.

(56) References Cited

U.S. PATENT DOCUMENTS

| | | | | |
|---|---|---|---|---|
| RE44,887 E | * | 5/2014 | Whitehouse | H01J 49/165 436/140 |
| 2003/0085125 A1 | * | 5/2003 | Prohaska | G01N 27/4071 204/424 |
| 2005/0266582 A1 | * | 12/2005 | Modlin | G01N 21/77 436/164 |
| 2012/0315191 A1 | * | 12/2012 | Maekawa | G01N 21/648 422/82.08 |
| 2017/0065959 A1 | * | 3/2017 | Urrutia | B65D 25/34 |
| 2018/0275105 A1 | | 9/2018 | Oki et al. | |

(Continued)

FOREIGN PATENT DOCUMENTS

| | | |
|---|---|---|
| JP | 2012-112724 A | 6/2012 |
| JP | 2018-155155 A | 10/2018 |

(Continued)

*Primary Examiner* — Matthew D Krcha
*Assistant Examiner* — Austin Q Le
(74) *Attorney, Agent, or Firm* — Oblon, McClelland, Maier & Neustadt, L.L.P.

(57) ABSTRACT

According to one embodiment, an apparatus for maintaining liquid membrane includes a liquid supply unit which supplies a liquid onto a sensor element and forms a liquid membrane, and a liquid discharge unit which discharges the liquid in the liquid membrane.

15 Claims, 5 Drawing Sheets

(56) References Cited

U.S. PATENT DOCUMENTS

| | | | |
|---|---|---|---|
| 2019/0112643 A1 | 4/2019 | Aran et al. | |
| 2019/0210021 A1* | 7/2019 | Waterman | B01L 3/502746 |
| 2019/0293596 A1* | 9/2019 | Nakamura | G01N 27/226 |
| 2019/0331661 A1* | 10/2019 | Zhen | A61B 5/082 |
| 2020/0086323 A1 | 3/2020 | Hongo et al. | |

FOREIGN PATENT DOCUMENTS

| | | |
|---|---|---|
| JP | 2018-155693 A | 10/2018 |
| JP | 2020-46263 A | 3/2020 |
| WO | WO 2017/149579 A1 | 9/2017 |

\* cited by examiner

APPARATUS FOR MAINTAINING LIQUID MEMBRANE AND SENSOR APPARATUS

CROSS-REFERENCE TO RELATED APPLICATIONS

This application is based upon and claims the benefit of priority from Japanese Patent Application No. 2019-168663, filed Sep. 17, 2019, the entire contents of which are incorporated herein by reference.

FIELD

Embodiments described herein relate generally to an apparatus for maintaining liquid membrane and a sensor apparatus.

BACKGROUND

There are sensors which detect odors, etc. There is demand for an apparatus which enables a sensor to perform detection with high accuracy.

DETAILED DESCRIPTION

In general, according to one embodiment, an apparatus for maintaining liquid membrane includes a liquid supply unit which supplies a liquid onto a sensor element and forms a liquid membrane, and a liquid discharge unit which discharges the liquid in the liquid membrane.

According to another embodiment, a sensor apparatus includes a sensor element, and the apparatus for maintaining liquid membrane of the one embodiment.

Hereinafter, various embodiments will be described with reference to the accompanying drawings. Each drawing is a schematic diagram for facilitating understanding of each embodiment, and a shape, a dimension, a proportion, and the like in the drawings may be different from actual ones. However, these can be appropriately modified in consideration of the following description and known technologies.

A sensor apparatus of an embodiment will be described below.

First Embodiment

Figure 1:
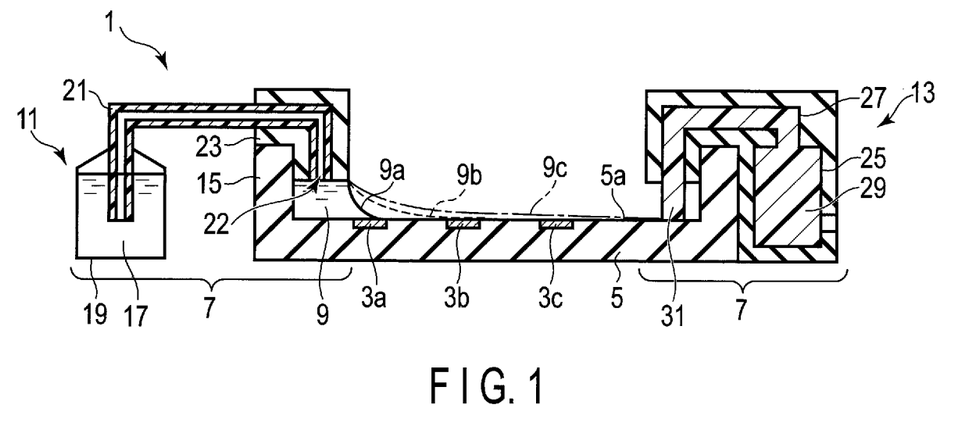
FIG. 1 is a cross-sectional view showing an example of a sensor apparatus of the first embodiment.
Figure 2:
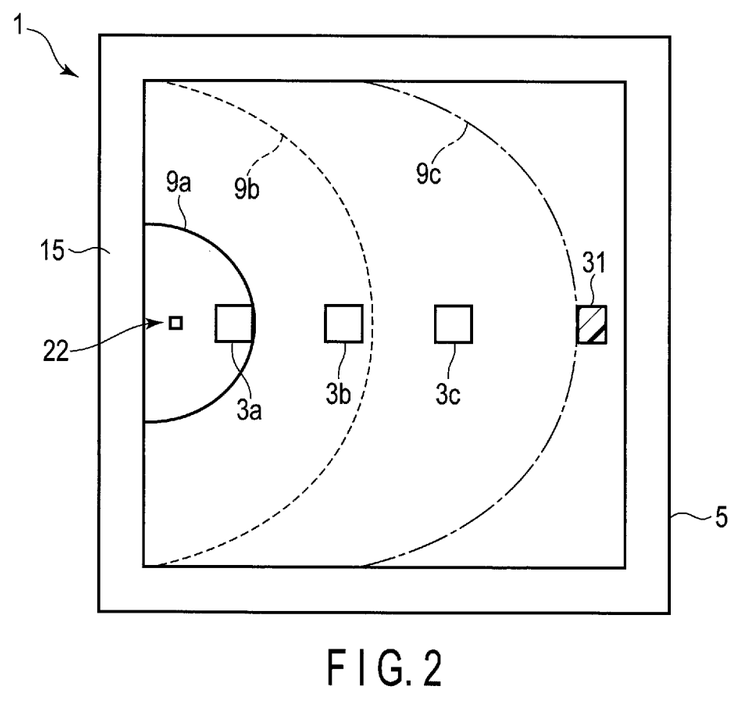
FIG. 2 is a plan view showing an example of the sensor apparatus of the first embodiment.

FIG. 1 is a cross-sectional view showing an example of a sensor apparatus of the first embodiment, and FIG. 2 is a plan view showing an example of the sensor apparatus of the first embodiment. Except for an opening 22 at the other end of a capillary 21 of a liquid supply unit 11, and a sensor element side end portion 31 of a first member 29 of a liquid discharge unit 13 shown in FIG. 1, the other configuration of an apparatus for maintaining liquid membrane 7 is omitted in FIG. 2.

As shown in FIG. 1, a sensor apparatus 1 includes a base 5 on which sensor elements 3a, 3b and 3c are arranged, and an apparatus for maintaining liquid membrane 7. The apparatus for maintaining liquid membrane 7 includes a liquid supply unit 11 which supplies a liquid onto the base 5 and forms a liquid membrane 9, and a liquid discharge unit 13 which discharges the liquid in the liquid membrane 9. The sensor elements 3a, 3b and 3c are graphene field effect transistors (referred to also as graphene FETs), and specific configurations thereof will be described later.

The base 5 is formed of, for example, an electrically insulating material. Examples of the insulating material of the base 5 include a polymer substance such as an acrylic resin, polyimide, polybenzoxazole, an epoxy resin, a phenol resin, polydimethylsiloxane, or fluorine resin, an inorganic insulating film such as silicon oxide, silicon nitride, or aluminum oxide, or a self-organized membrane of an organic molecule. A surface 5a of the base 5 has hydrophilicity (for example, a drop of liquid which is in contact with the surface has a contact angle of less than 5 degrees). A size of the base 5 is not limited. For example, a width of the base 5 is 1 to 100 mm, a length of the base 5 is 1 to 100 mm, a thickness of the base 5 is 1 to 5 mm.

Wall portions 15 which extend upward are disposed around the periphery of the base 5. The wall portions 15 surround the sensor elements 3a, 3b and 3c in planar view. Here, the planar view means viewing the base 5 from above a side of the base 5 on which the sensor elements 3a, 3b and 3c are arranged. The wall portions 15 define a region in which a liquid membrane is formed.

The liquid supply unit 11 includes a first container (bottle) 19 which is spaced apart from the wall portions 15 of the base 5 and accommodates a liquid 17. One end of the capillary 21 is in contact with the liquid 17 accommodated in the bottle 19. The other end of the capillary 21 is fixed by a fixing member 23 in a state where an opening 22 faces the surface 5a of the base 5 above the sensor element 3a side of the base 5. The liquid supply unit 11 supplies the liquid 17 in the bottle 19 through the capillary 21, and forms the liquid membrane 9 on the sensor elements 3a, 3b and 3c arranged on the base 5.

The liquid 17 is a liquid supply source for forming the liquid membrane 9 on the sensor elements 3a, 3b and 3c arranged on the base 5. The liquid 17 is, for example, a water-soluble liquid such as water, physiological water, or buffer solution, or an ionic liquid. The liquid 17 may contain an organic solvent.

The capillary 21 is formed of, for example, a material such as polymer or glass, and the inner surface of the capillary 21 has hydrophilicity. The inner diameter of the capillary 21 is, for example, 0.10 mm to 10.0 mm. The capillary 21 sends the liquid 17 in the bottle 19 onto the sensor elements 3a, 3b and 3c arranged on the base 5 using capillary phenomenon, for example. The liquid is supplied onto the base 5 by the capillary 21 at a supply flow rate of, for example, 0.01 μL/s to 1.0 μL/s. It is possible to adjust the supply flow rate of the capillary 21 by, for example, changing the inner diameter of the capillary 21.

The liquid discharge unit 13 includes a discharge liquid collection space 25 which is adjacent to the wall portions 15 of the base 5 and collects the liquid discharged from the liquid membrane 9. In the discharge liquid collection space 25, one end side opening of a discharge liquid flow passage 27 is formed. The other end side opening of the discharge liquid flow passage 27 is arranged above the sensor element 3c side of the base 5. The discharge liquid collection space 25 and the discharge liquid flow passage 27 are filled with a first member 29. A sensor element side end portion 31 of the first member 29 is in contact with a sensor element 3c side surface of the base 5. The sensor element side end portion 31 is in contact with the liquid membrane 9. The liquid discharge unit 13 moves the liquid in the liquid membrane 9 to the discharge liquid collection space 25 through the discharge liquid flow passage 27.

The discharge liquid collection space 25 collects the liquid discharged from the liquid membrane 9. The discharge liquid flow passage 27 moves the liquid discharged from the liquid membrane 9 to the discharge liquid collection space 25. The discharge liquid collection space 25 and the discharge liquid flow passage 27 are formed by, for example, processing and shaping the same material as the base 5.

The material of the first member 29 is, for example, a non-woven fabric of sodium polyacrylate, polyethylene, polystyrene, cellulose, or the like. A non-woven fabric of cellulose is a cellulose pad for lateral flow immuno-assay (LFIA). The first member 29 moves the liquid in the liquid membrane 9 to the discharge liquid collection space 25 through the discharge liquid flow passage 27 using, for example, capillary phenomenon. The liquid in the liquid membrane 9 is discharged (absorbed) by the first member 29 at a discharge rate (water absorption rate) of, for example, 0.01 μL/s to 1.0 μL/s. It is possible to adjust the water absorption rate of the first member 29 by, for example, changing the cross-sectional area of the first member 29. Here, the cross-sectional area of the first member 29 means the contact area of the sensor element side end portion 31 with the surface of the base 5. The cross-sectional area of the first member 29 is, for example, 0.10 mm$^2$ to 10 mm$^2$. The volume of the first member 29 is, for example, 2.0 cm$^3$ to 5.0 cm$^3$.

In some embodiments, the first member 29 is arranged on a line which connects the liquid supply unit 11 and the sensor elements 3a, 3b and 3c. By the first member 29 arranged as described above, the liquid membrane 9 to be formed by the liquid supply unit 11 is spread over the sensor elements 3a, 3b and 3c. Therefore, it is possible to carry a gas sample 49 which will be described later to the sensor elements 3a, 3b and 3c using the liquid membrane 9 as a medium.

When the cross-sectional area of the first member 29 is, for example, 0.83 mm$^2$, the water absorption rate of the first member 29 is 0.10 μL/s. When the cross-sectional area of the first member 29 is 1.66 mm$^2$, the water absorption rate of the first member 29 is 0.30 μL/s. When the cross-sectional area of the first member 29 is 3.32 mm$^2$, the water absorption rate of the first member 29 is 0.40 μL/s. When the cross-sectional area of the first member 29 is small, the water absorption rate of the first member 29 can be easily controlled. The volume of the first member 29 filling the discharge liquid collection space 25 is, for example, 2.0 cm$^3$ to 5.0 cm$^3$.

As the liquid supply unit 11 supplies the liquid 17 in the bottle 19 onto the sensor element 3a side of the base 5 using the capillary phenomenon of the capillary 21, the apparatus for maintaining liquid membrane 7 forms a liquid membrane 9a. In other words, the liquid supply unit 11 forms the liquid membrane 9a on a sensitive membrane 35 which will be described later of the sensor element 3a. Then, the liquid supply unit 11 further supplies the liquid 17 in the bottle 19 to the sensor element 3a side of the base 5 and forms a liquid membrane 9b which spreads substantially in a circle toward the liquid discharge unit 13. Then, the liquid supply unit 11 further supplies the liquid 17 in the bottle 19 to the sensor element 3a side of the base 5 and forms a liquid membrane 9c which further spreads substantially in a circle toward the liquid discharge unit 13. Then, the liquid discharge unit 13 absorbs the liquid in the liquid membrane 9c which is in contact with the sensor element side end portion 31 of the first member 29. The absorbed liquid is moved to the discharge liquid collection space 25 through the discharge liquid flow passage 27 by the first member 29. After the liquid is absorbed from the liquid membrane 9c, the liquid membrane 9c returns to the liquid membrane 9a. Consequently, the apparatus for maintaining liquid membrane 7 can form and maintain the liquid membrane 9, which changes as the liquid flows with time (the liquid membranes 9a, 9b and 9c shown in FIGS. 1 and 2), on the sensor elements 3a, 3b and 3c arranged on the base 5. Here, the maintaining of the liquid membrane 9 by the apparatus for maintaining liquid membrane 7 means that the apparatus for maintaining liquid membrane 7 adjusts the liquid membrane 9 to any one state from the liquid membrane formed on the liquid supply unit 11 side (for example, the liquid membrane 9a shown in FIGS. 1 and 2) to the liquid membrane spreading toward the liquid discharge unit 13 (for example, the liquid membrane 9c shown in FIGS. 1 and 2).

The liquid membrane 9 is, for example, a water-soluble liquid such as water, physiological water, or buffer solution, or an ionic liquid. The liquid membrane 9 may contain an organic solvent. The thickness of the liquid membrane 9 is, for example, greater than or equal to 1.0 μm but less than or equal to 10.0 μm. The thickness of the liquid membrane 9 is, for example, the shortest distance from the surface of the base 5 or the surfaces of the sensor elements 3a, 3b and 3c to the interface between the liquid membrane 9 and the gas. For example, the liquid membrane 9 functions as a medium which carries a target substance 51 which will be described later to a receptor 47.

The sensor elements 3a, 3b and 3c are graphene FETs and have the same structure. In the following, the sensor element 3a will be described as a representative example.

Figure 3:
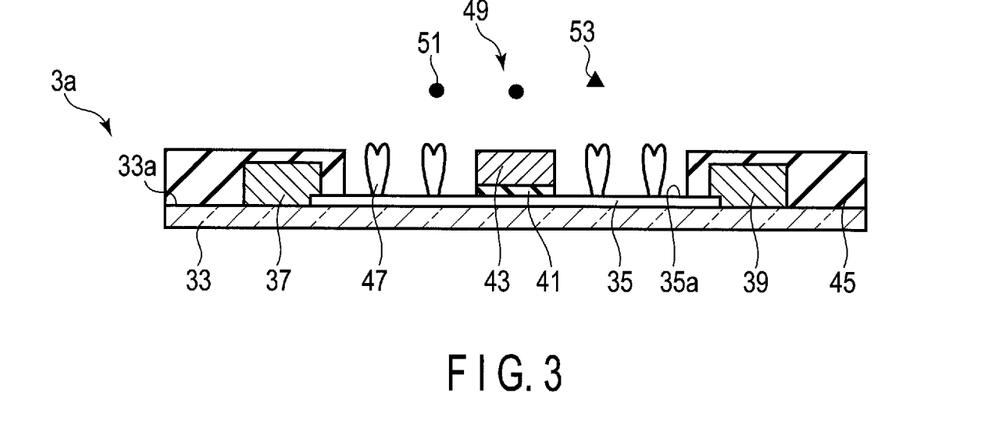
FIG. 3 is a cross-sectional view showing an example of a sensor element of the embodiment.

As shown in FIG. 3, the sensor element 3a includes a substrate 33. A sensitive membrane 35, a source electrode 37 connected to one end of the sensitive membrane 35, and a drain electrode 39 connected to the other end of the sensitive membrane 35 are disposed on a surface 33a of the substrate 33. A gate electrode 43 is disposed on a surface 35a of the sensitive membrane 35 via a first insulating layer 41 between the source electrode 37 and the drain electrode 39. A second insulating layer 45 is disposed on the surface 33a of the substrate 33. The receptor 47 is connected to the surface 35a of the sensitive membrane 35. The receptor 47 is in contact with the liquid membrane 9 or is immersed in the liquid membrane 9.

The substrate 33 has, for example, a rectangular plate shape. The substrate 33 is formed of, for example, silicon, glass, ceramic, a polymer material, metal, or the like. A size of the substrate 33 is not limited. For example, a width of the substrate 33 is 1 to 10 mm, a length of the substrate 33 is 1 to 10 mm, and a thickness of the substrate 33 is 0.1 to 0.5 mm.

The sensitive membrane 35 is a membrane whose physical properties change as the structure of a substance connected thereto, the state of electric charge, or the like changes. The sensitive membrane 35 is formed of, for example, a substance whose electric resistance changes. The sensitive membrane 35 is a single-layer graphene membrane having a thickness corresponding to one carbon atom. As the graphene membrane, a multi-layer graphene membrane may also be provided. A size of the sensitive membrane 35 is not limited. For example, a width of the membrane 35 can be 1 to 500 µm, a length of the sensitive membrane 35 can be 1 to 500 µm. In practice, when the width of the membrane 35 is 10 to 100 µm and the length of the membrane 35 is 10 to 100 µm, the membrane 35 can be easily produced.

The sensitive membrane 35 may be formed of, for example, a membrane of a conductor such as polymer, silicon (Si), or silicide, or nanowire thereof, or a material such as graphene, carbon nanotube, molybdenum disulfide ($MoS_2$), or tungsten diselenide ($WSe_2$).

The source electrode 37, the drain electrode 39 and the gate electrode 43 are formed of, for example, metal such as gold (Au), silver (Ag), copper (Cu), palladium (Pd), platinum (Pt), nickel (Ni), titanium (Ti), chromium (Cr) or aluminum (Al) or a conductive substance such as zinc oxide (ZnO), indium tin oxide (ITO), indium gallium zinc oxide semiconductor (IGZO), or conductive polymer.

The source electrode 37, the drain electrode 39 and the gate electrode 43 are electrically connected to a power supply (not shown). For example, when a voltage (source-drain voltage ($V_{sd}$)) is applied from the power supply to the source electrode 37 and the drain electrode 39 under a constant gate voltage, a current (source-drain current ($I_{sd}$)) flows from the source electrode 37 to the drain electrode 39 via the sensitive membrane 35. At this time, the sensitive membrane 35, which is a graphene membrane, functions as a channel with respect to the source electrode 37 and the drain electrode 39. The gate electrode 43 changes the source-drain current by changing the gate voltage.

The first insulating layer 41 is formed of, for example, an electrically insulating material such as oxide, nitride or oxynitride of silicon, gallium, aluminum and indium, a polymer material, or a self-assembled membrane of organic molecules. The thickness of the first insulating layer 41 should preferably be reduced as much as possible within a range in which insulating properties are not impaired, and should preferably be, for example, about several nanometers. Such a thin membrane can be formed by, for example, an atomic layer deposition (ALD) method.

The second insulating layer 45 is formed of, for example, the same material as the above-described base 5.

The receptor 47 is, for example, a biological substance. For example, a fragment of an olfactory receptor can be used as the receptor 47. The receptor 47 is a fragment of an olfactory receptor including a sequence of a site which binds to the target substance 51 in the gas sample 49. For example, the sequence includes a ligand binding site located on the outside of the cell of the olfactory receptor. It is possible to produce the receptor 47 by, for example, obtaining an amino acid sequence of the ligand binding site from a olfactory receptor database and synthesizing oligopeptide having the amino acid sequence. The receptor 47 may be a substance binding to the target substance 51, for example, may be a substance of which a sequence of a ligand binding site is partially changed, or may be a substance to which a new sequence is added. The receptor 47 can use, for example, the olfactory receptor of an animal as the olfactory receptor. Examples of the animal are vertebrates, insects, and the like. For example, the olfactory receptor of a human, a mouse, a fly, a nematode, or the like can be used.

The receptor 47 may be a substance binding to the target substance 51 and may be, for example, an antibody or a nucleic acid aptamer or may be an artificial object such as a molecular imprint. When the receptor 47 is an artificial object such as a molecular imprint, the receptor 47 is less likely to be deformed or damaged by dryness.

The receptor 47 can be fixed on the sensitive membrane 35 by, for example, adding a modified group to the receptor 47 and/or the sensitive membrane 35, and binding the modified group and the receptor 47 and/or the sensitive membrane 35 to each other through chemical synthesis. It is also possible to connect the receptor 47 to the sensitive membrane 35 by disposing the receptor 47 on the surface 35a of the sensitive membrane 35. It is also possible to connect the receptor 47 to the sensitive membrane 35 such as a graphene membrane by π-π interactions.

In addition to the receptor 47, a blocking agent (not shown) may be disposed on the surface 35a of the sensitive membrane 35 so as to cover the surface 35a. For example, protein, organic molecule, lipid membrane, peptide, nucleic acid, or the like can be used as the blocking agent. By providing the blocking agent, it is possible to prevent a substance different from the target substance 51 (for example, impurities 53) from binding to the surface of the sensitive membrane 35.

The target substance 51 is a substance which is contained in the gas and may serve as the ligand of the olfactory receptor of an animal. The target substance 51 is, for example, a volatile organic compound (VOC) such as an odor substance or a pheromone substance. Examples of the target substance 51 are alcohols, esters, aldehydes, ketones, and the like, but the target substance 51 is not limited to these examples. Most of these examples of the target substance 51 are substances having low water solubility. The target substance 51 having low water solubility is, for example, such a substance that the liquid membrane 9 of greater than or equal to 1 µl is required for dissolving the target substance 51 of 0.1 mg.

The gas sample 49 is, for example, a gas which is to be analyzed and may contain the target substance 51. The gas sample 49 is, for example, air, an exhalation, another gas which may be generated from an analysis target such as a living body or an object, or air around the analysis target. The gas sample 49 may contain the impurities 53.

The detection of the target substance by the sensor elements 3a, 3b and 3c includes, for example, the following steps. That is, (S1) the sensor apparatus of the embodiment is prepared, (S2) the gas sample is brought into contact with the liquid membrane or the receptor, (S3) a change in the physical properties of the sensitive membrane is detected, and (S4) the presence or absence or the amount of the target substance in the gas sample is determined from the detection result.

Hereinafter, a principle according to which the target substance is detected by performing the respective processes will be described.

Figure 4:
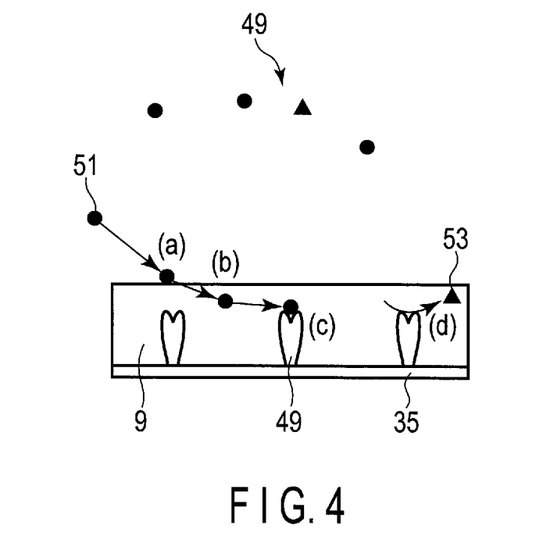
FIG. 4 is a schematic view showing a state of the sensor element of the embodiment when the sensor element is detecting target substance.
Figure 5:
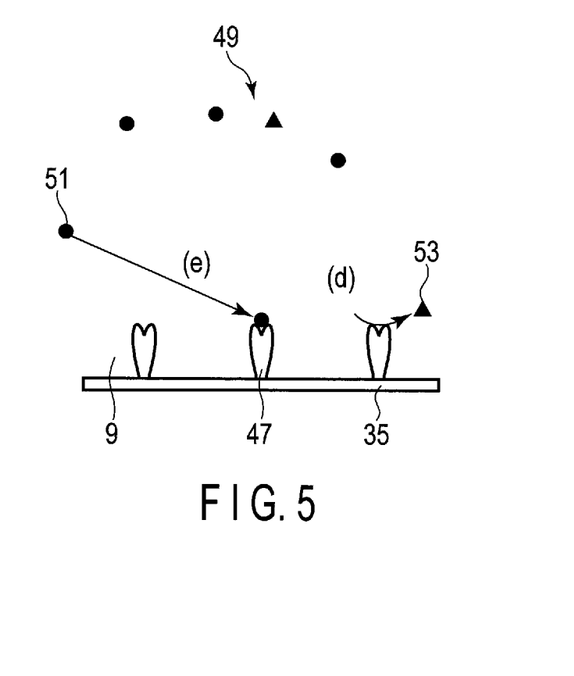
FIG. 5 is a schematic view showing another state of the sensor element of the embodiment when the sensor element is detecting target substance.

In step S2, the gas sample 49 is brought into contact with the liquid membrane 9 or the receptor 47. The state of the sensor element 3 at this time is shown in FIGS. 4 and 5. FIG. 4 shows a state where the liquid membrane 9 exists on the receptor 47. In other words, FIG. 4 shows the sensor element 3a below the liquid membrane 9a, the sensor element 3b below the liquid membrane 9b, or the sensor element 3c below the liquid membrane 9c. In addition, FIG. 5 shows a state where the liquid membrane 9 does not exist on the receptor 47. In other words, FIG. 5 shows the sensor element 3b or the sensor element 3c in a situation where the liquid membrane 9 is in the state of the liquid membrane 9a or the sensor element 3c in a situation where the liquid membrane 9 is in the state of the liquid membrane 9b.

In FIG. 4, the gas sample 49 contacts the liquid membrane 9 and the target substance 51 enters the liquid membrane 9 ((a) and (b) of FIG. 4), and the target substance 51 binds to the receptor 47 ((c) of FIG. 4). On the other hand, the impurities 53 do not bind to the receptor 47 ((d) of FIG. 4). When the target substance 51 binds to the receptor 47 ((c) of FIG. 4), the physical properties of the sensitive membrane 35 change.

In FIG. 5, the target substance 51 of the gas sample 49 directly reaches the receptor 47 and binds to the receptor 47 ((e) of FIG. 5). The impurities 53 do not bind to the receptor 47 ((d) of FIG. 5). The physical properties here are, for example, the electric resistance of the sensitive membrane, and the like.

In step S3, the change in physical properties is detected as a change in electric signal. The electric signal is, for example, a current value, a potential value, an electric capacitance value, an impedance value, or the like. The change in the electric signal is, for example, an increase or a decrease in the electric signal, a loss of the electric signal, a change in the integrated value within a certain time in the electric signal, or the like. In the case of using the graphene FET described above, the change in the physical properties can be detected as, for example, a change in source-drain current value which occurs when a constant voltage is applied as a gate voltage and a drain voltage. Alternatively, the change in the physical properties can be detected as a change in gate voltage value which occurs when a source-drain current value is kept constant. For example, information about the change in the electric signal is transmitted to, stored in, and processed by an electrically connected data processing unit or the like.

In step S4, the presence or absence or the amount of the target substance 51 in the gas sample 49 is determined from the detection result. For example, the target substance 51 may be determined to be present in the gas sample 49 when the electric signal changes, and the target substance 51 may be determined to be absent when the electric signal does not change. Alternatively, the target substance 51 may be determined to be present when the change in the electric signal is greater than a preset threshold value, and the target substance 51 may be determined to be absent when the change is less than the threshold value. It is possible to obtain the threshold value by, for example, subjecting a gas sample known to contain the target substance to the analysis of the sensor element and obtaining the value of a change in electric signal. Alternatively, the amount of the target substance may be determined according to the amount of change. In that case, a calibration curve of the amount of change with respect to the concentration of the target substance may be created using the target substance whose concentration is known, and the amount of the target substance may be determined with reference to the calibration curve.

According to the above-described steps, the sensor elements 3a, 3b and 3c can detect the target substance in the gas sample.

The method of detecting the target substance may be performed by an apparatus which automatically performs each step. The apparatus includes, for example, a sensor apparatus 1, a detection unit which converts a change in the physical properties of the sensitive membrane 35 to a change in electric signal, a data processing unit which stores and processes information about the electric signal obtained from the detection unit, and a control unit which controls the operation of each of these units. The operations in steps S2 to S4 described above may be executed by inputs of the operator of the apparatus or may be executed by programs included in the control unit.

These sensor elements 3a, 3b and 3c are not limited to graphene FETs. When a biological substance such as the receptor 47, an antibody, a nucleic acid aptamer, or an artificial object such as a molecular imprint is used as each of the sensor elements 3a, 3b and 3c, each of the sensor elements 3a, 3b and 3c can be a sensor element such as another electric charge detection element, a surface plasmon resonance (SPR) element, a surface acoustic wave (SAW) element, a film bulk acoustic resonance (FBAR) element, a quartz crystal microbalance (QCM) element or a microelectromechanical systems (MEMS) cantilever element.

Since the sensor apparatus 1 of the first embodiment includes the apparatus for maintaining liquid membrane 7, the liquid membrane 9 which changes as the liquid flows with time (the liquid membranes 9a, 9b and 9c shown in FIGS. 1 and 2) can be formed and maintained on the sensor elements 3a, 3b and 3c arranged on the base 5 by the apparatus 7. The sensor element 3a arranged below the liquid membrane 9a can detect the target substance 51 with high accuracy since performance degradation in the detection of the target substance 51 caused by dryness of the receptor 47 is suppressed or prevented. The sensor element 3a described above is more likely to detect the water-soluble target substance 51. Here, the water-soluble target substance 51 is, for example, such a substance that the liquid membrane 9 of less than or equal to 1 µl is required for dissolving the target substance 51 of 1.0 mg. In addition, the sensor elements 3b and 3c arranged below the liquid membranes 9b and 9c can quickly detect the target substance 51 since the target substance 51 is more likely to directly reach the sensor element 3 without passing through the liquid membrane 9 and detect the target substance 51 with high accuracy even when the concentration of the target substance 51 is low. Furthermore, the sensor elements 3b and 3c can detect the target substance 51 having low water solubility as described above.

Therefore, an apparatus for maintaining liquid membrane of the first embodiment enables the sensor element to detect the target substance with high accuracy. In addition, since the sensor apparatus of the first embodiment includes the above-described apparatus for maintaining liquid membrane, the sensor apparatus can detect the target substance with high accuracy.

Furthermore, since the apparatus for maintaining liquid membrane of the first embodiment can repeatedly form a new liquid membrane and maintain the liquid membrane, the apparatus for maintaining liquid membrane of the first embodiment enables the sensor element to repeatedly detect the target substance. Furthermore, since the sensor apparatus of the first embodiment includes the above-described apparatus for maintaining liquid membrane, the sensor apparatus of the first embodiment can repeatedly detect the target substance.

Furthermore, since the sensor apparatus of the first embodiment includes the sensor element having the receptor which binds to the target substance, the sensor apparatus of the first embodiment can prevent impurities from being detected. Therefore, it is possible to detect the target substance without being influenced by the impurities even under a condition where the composition of the substance contained in the gas sample varies.

Sensor apparatuses of other embodiments will be described hereinafter with reference to FIGS. 6 to 10. The same members as those shown in FIG. 1 will be denoted by the same reference numbers in FIGS. 6 to 10, and descriptions thereof will be omitted.

Second Embodiment

Figure 6:
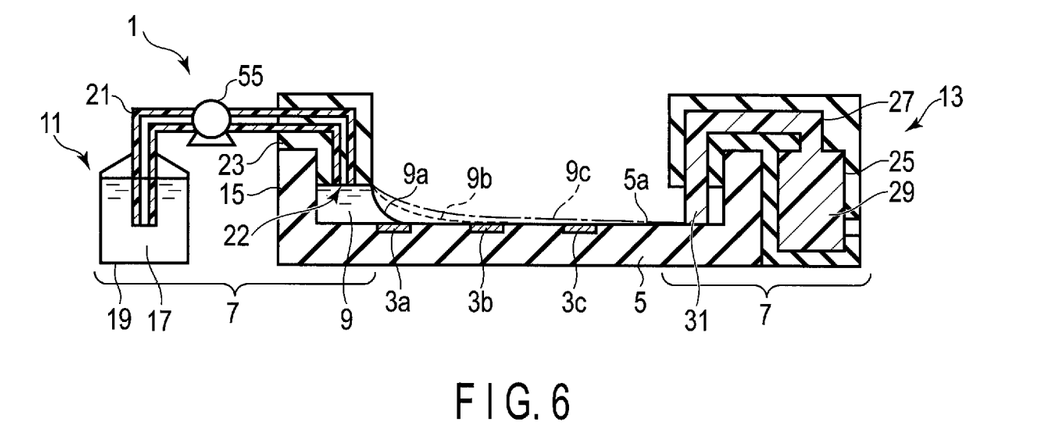
FIG. 6 is a cross-sectional view showing an example of a sensor apparatus of the second embodiment.

FIG. 6 is a cross-sectional view showing an example of the sensor apparatus of the second embodiment. The sensor apparatus 1 shown in FIG. 6 has the same structure as the sensor apparatus shown in FIG. 1 except that the sensor apparatus 1 shown in FIG. 6 includes a pump 55.

The liquid supply unit 11 of the apparatus for maintaining liquid membrane 7 of the second embodiment further includes a pump 55. The pump 55 is attached to the capillary 21 and can supply the liquid 17 in the bottle 19 onto the sensor elements 3a, 3b and 3c arranged on the base 5 at an arbitrarily supply flow rate. The pump 55 can be set to a supply flow rate of, for example, 0.01 µL/s to 1.0 µL/s. It is possible to prevent a liquid leakage caused by an oversupply by setting the pump 55 to a supply flow rate lower than a discharge rate at which the liquid in the liquid membrane is discharged by the liquid discharge unit 13, that is, the water absorption rate of the first member 29 of the liquid discharge unit 13.

Since the sensor apparatus 1 of the second embodiment includes the apparatus for maintaining liquid membrane 7 having the pump 55, the liquid membrane 9 which changes as the liquid periodically flows with time is formed and maintained on the sensor elements 3a, 3b and 3c arranged on the base 5 by the apparatus 7. Therefore, noise which may occur as the liquid membrane 9 passes over the sensor elements 3b and 3c arranged below the liquid membrane 9b or 9c appears periodically. Consequently, the sensor apparatus 1 of the second embodiment can easily determine whether the receptor 47 has detected the target substance 51 or not and detect the target substance 51 with higher accuracy.

In addition, the apparatus for maintaining liquid membrane 7 having the pump 55 can increase the measurement time by reducing the supply flow rate. Furthermore, the apparatus for maintaining liquid membrane 7 can reduce the amount of the accommodated liquid 17 and the amount of the filled first member 29 of the liquid discharge unit 13 by reducing the supply flow rate.

Therefore, the apparatus for maintaining liquid membrane of the second embodiment produces the same function and effect as the apparatus for maintaining liquid membrane of the first embodiment, enables the sensor element to perform detection with high accuracy for a long time, and contributes to miniaturizing the sensor element. In addition, since the sensor apparatus of the second embodiment produces the same function and effect as the sensor apparatus of the first embodiment and includes the above-described apparatus for maintaining liquid membrane, the sensor apparatus of the second embodiment can detect the target substance with high accuracy for a long time, and the sensor apparatus of the second embodiment can be miniaturized.

Third Embodiment

Figure 7:
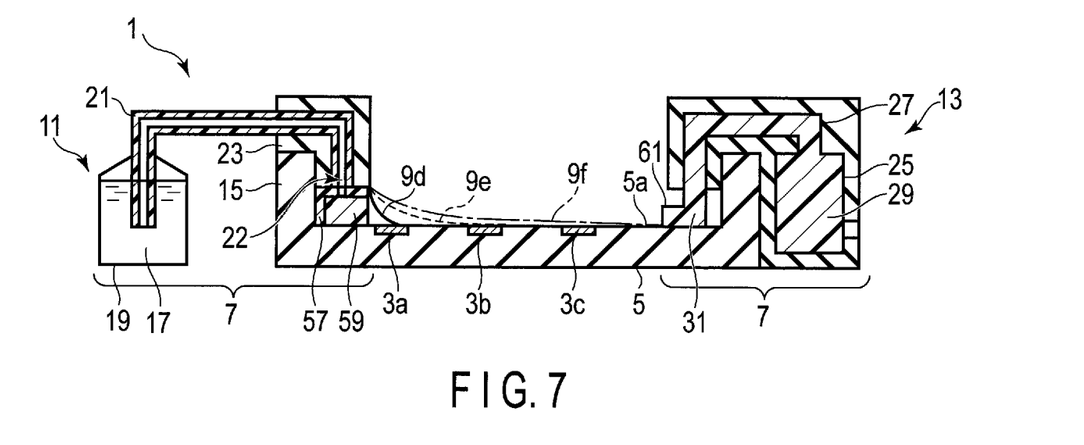
FIG. 7 is a cross-sectional view showing an example of a sensor apparatus of the third embodiment.
Figure 8:
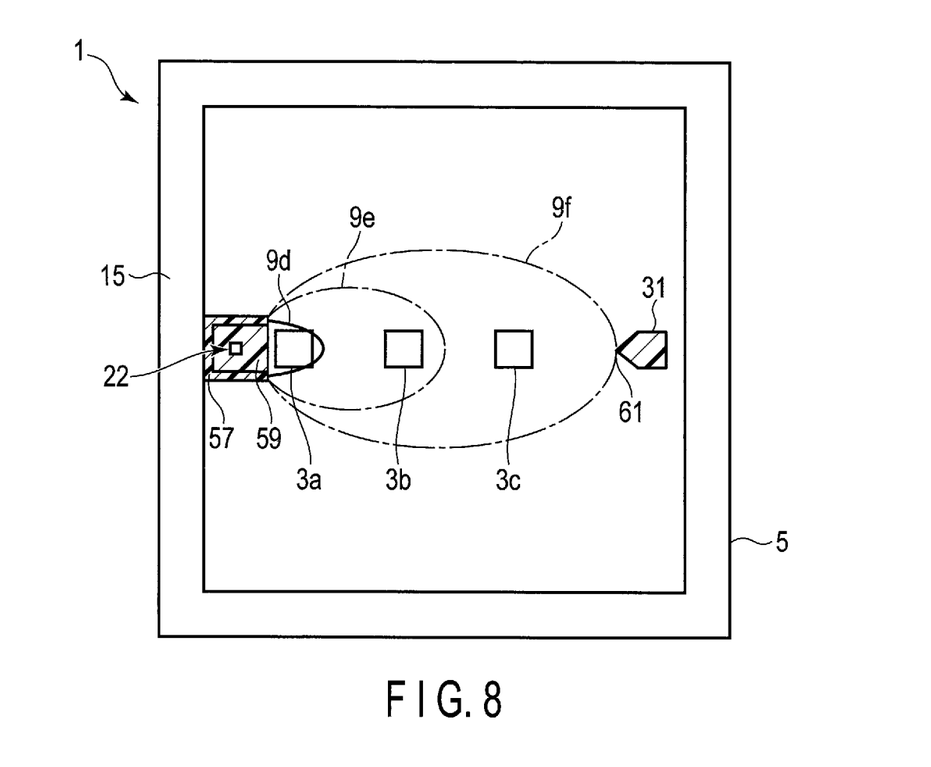
FIG. 8 is a plan view showing an example of a sensor apparatus of the third embodiment.

FIG. 7 is a cross-sectional view showing an example of a sensor apparatus of the third embodiment, and FIG. 8 is a plan view showing an example of the sensor apparatus of the third embodiment. Except for the opening 22 at the other end side of the capillary 21 of the liquid supply unit 11, a flow control unit 57, a liquid retention member 59, the sensor element side end portion 31 of the first member 29 of the liquid discharge unit 13, and a protrusion portion 61 shown in FIG. 7, the other configuration of the apparatus for maintaining liquid membrane 7 is omitted in FIG. 8.

The liquid supply unit 11 of the apparatus for maintaining liquid membrane 7 of the third embodiment further includes a flow control unit 57 which communicates with the opening 22 of the capillary 21, and a liquid retention member 59 disposed in the flow control unit 57. In addition, the liquid discharge unit 13 of the apparatus for maintaining liquid membrane 7 of the third embodiment further includes a protrusion portion 61, more specifically, the sensor element side end portion 31 of the first member 29 protrudes toward the liquid supply unit 11.

The flow control unit 57 is attached so as to communicate with the opening 22 of the capillary 21, and has the shape of letter U which is open on the liquid discharge unit 13 side in planar view. The flow control unit 57 may be formed of, for example, the same material as the above-described base 5. A size of the flow control unit 57 is not limited. For example, a width of the flow control unit 57 is 1 to 10 mm, a length of the flow control unit 57 is 1 to 10 mm, a height of the flow control unit 57 is 1 to 10 mm. The surface of the flow control unit 57 has, for example, hydrophilicity. The flow control unit 57 makes the liquid 17 supplied from the bottle 19 onto the sensor elements 3a, 3b and 3c arranged on the base 5 flow toward the liquid discharge unit 13, and forms the liquid membrane 9 (9d, 9e and 9f) which spreads less as compared to the apparatus for maintaining liquid membrane 7 of the first embodiment, and controls the flow of the liquid.

The liquid retention member 59 retains the liquid supplied from the liquid supply unit 11. The liquid retention member 59 is formed of, for example, the same material as the above-described first member 29.

In some embodiments, the liquid retention member 59 is arranged on a line which connects the liquid discharge unit 13 and the sensor elements 3a, 3b and 3c. By the liquid retention member 59 arranged as described above, the liquid membrane 9 formed by the liquid supply unit 11 is spread over the sensor elements 3a, 3b and 3c. Therefore, it is possible to carry a gas sample 49 which will be described later onto the sensor elements 3a, 3b and 3c using the liquid membrane 9 as a medium.

Since the sensor apparatus 1 of the third embodiment includes the apparatus for maintaining liquid membrane 7 including the flow control unit 57, the liquid retention member 59 and the protrusion portion 61, the liquid membrane 9 (9d, 9e and 9f) which changes while spreading less is formed and maintained on the sensor elements 3a, 3b and 3c arranged on the base 5 by the apparatus 7. Therefore, the apparatus for maintaining liquid membrane 7 can reduce the amount of the accommodated liquid 17 and the amount of the filled first member 29 of the liquid discharge unit 13.

The liquid supply unit 11 including the flow control unit 57 suppresses or prevents accumulation of the liquid 17 supplied from the bottle 19 to the sensor elements 3a, 3b and 3c arranged on the base 5 in the vicinity of the opening 22 of the liquid supply unit 11. In addition, the liquid supply unit 11 including the liquid retention member 59 further suppresses or prevents accumulation of the liquid 17 supplied from the bottle 19 to the sensor elements 3a, 3b and 3c arranged on the base 5 in the vicinity of the opening 22 of the liquid supply unit 11. Therefore, the apparatus for maintaining liquid membrane 7 can detect the target substance 51 with higher accuracy by suppressing or preventing such a situation where the target substance 51 is accumulated in the vicinity of the opening 22 of the liquid supply unit 11 without passing over the sensor elements 3a, 3b and 3c and the sensor elements 3a, 3b and 3c fail to detect the target substance 51.

Consequently, the apparatus for maintaining liquid membrane of the third embodiment produces the same function and effect as the apparatus for maintaining liquid membrane of the first embodiment, and enables the sensor element to perform detection with higher accuracy for a long time. In addition, since the sensor apparatus of the third embodiment produces the same function and effect as the sensor apparatus of the first embodiment and includes the above-described apparatus for maintaining liquid membrane, the sensor apparatus of the third embodiment can detect the target substance with high accuracy for a long time.

Fourth Embodiment

Figure 9:
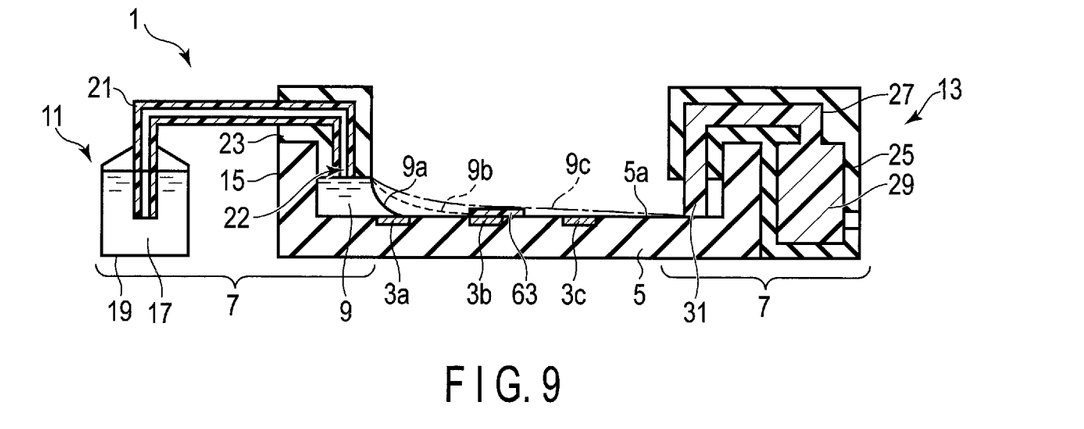
FIG. 9 is a cross-sectional view showing an example of a sensor apparatus of the fourth embodiment.

FIG. 9 is a cross-sectional view showing an example of a sensor apparatus of the fourth embodiment. The sensor apparatus 1 shown in FIG. 9 has the same structure as the sensor apparatus shown in FIG. 1 except that a liquid retention layer 63 is disposed on part of the surface 5a of the base 5 and the sensor element 3b.

The liquid retention layer 63 of the fourth embodiment covers part of the surface 5a of the base 5 and the surface of the sensor element 3b. The thickness of the liquid retention layer 63 is, for example, 1.0 μm to 100 μm. The liquid retention layer 63 can always keep the surface 5a of the base 5 and the sensor element 3b below the liquid retention layer 63 wet. The liquid retention layer 63 may cover part of the surface 5a of the base 5 or may cover the entire surface 5a of the base 5.

Since the sensor apparatus 1 of the fourth embodiment includes the liquid retention layer 63, the sensor apparatus 1 of the fourth embodiment can always keep an arbitrary position on the surface 5a of the base 5 and/or the sensor elements 3a, 3b and 3c wet. Therefore, performance degradation in the detection of the target substance 51 caused by dryness of the receptor 47 is suppressed or prevented, and the sensor element 3b arranged below the liquid retention layer 63 can detect the target substance 51 with high accuracy.

Since the sensor apparatus of the fourth embodiment produces the same function and effect as the sensor apparatus of the first embodiment and includes the above-described liquid retention layer 63, the sensor apparatus of the fourth embodiment can detect the target substance with higher accuracy.

Fifth Embodiment

Figure 10:
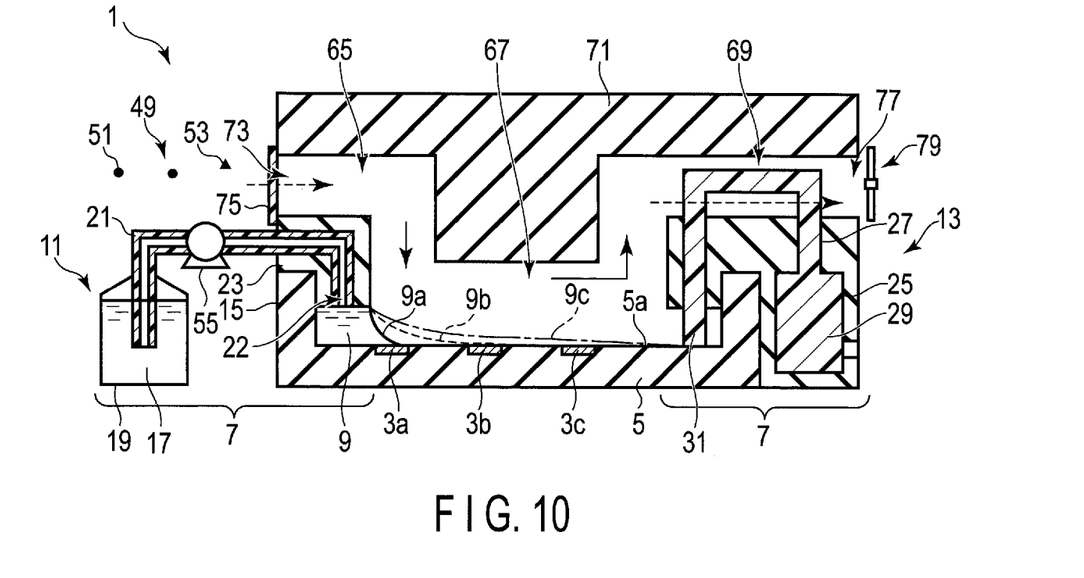
FIG. 10 is a cross-sectional view showing an example of a sensor apparatus of the fifth embodiment.

FIG. 10 is a cross-sectional view showing an example of a sensor apparatus of the fourth embodiment. The sensor apparatus shown in FIG. 10 has the same structure as the sensor apparatus shown in FIG. 1 except that a pump 55 is disposed, a cover member 71 defining a first flow passage 65, a second flow passage 67 and a third flow passage 69 is disposed above the base 5, a filter 75 is disposed in an inlet 73 of the first flow passage 65, an airflow generation apparatus 79 is disposed in an outlet 77 of the third flow passage 69, and part of the first member 29 of the liquid discharge unit 13 is arranged in the third flow passage 69.

As shown in FIG. 10, a first flow passage 65, a second flow passage 67 and a third flow passage 69 are defined by a cover member 71 which is disposed above the sensor apparatus 1 and is spaced apart from the sensor apparatus 1. A filter 75 is disposed in an inlet 73 of the first flow passage 65. An airflow generation apparatus 79 is disposed in an outlet 77 of the third flow passage 69. Part of the first member 29 of the liquid discharge unit 13 is arranged in the third flow passage 69.

The first flow passage 65, the second flow passage 67 and the third flow passage 69 communicate with one another. The first flow passage 65 is a flow passage which takes in the gas sample 49, the second flow passage 67 is a flow passage which introduces the taken gas sample 49 into the sensor elements 3a, 3b and 3c arranged on the base 5, and the third flow passage 69 is a flow passage which sends the untaken gas sample 49 to the outside of the sensor apparatus 1. The cover member 71 is formed of, for example, the same material as the above-described base 5. The filter 75 prevents entry of dust into the flow passage.

In the third flow passage 69, the first member 29 of the liquid discharge unit 13 arranged therein has the shape of a strip of 0.83 mm$^2$×280 mm (cross-sectional area×length), for example. The first member 29 described above is bent in the third flow passage 69, for example. In the third flow passage, the first member 29 evaporates and dries the absorbed liquid. Therefore, the amount of the filled first member 29 of the liquid discharge unit 13 can be reduced.

The airflow generation apparatus 79 is, for example, a fan. The airflow generation apparatus 79 generates a flow of air flowing from the first flow passage 65, passing through the second flow passage 67, and flowing to the third flow passage 69. It is possible to take the gas sample 49 into the first flow passage 65 by the airflow. It is also possible to dry the first member 29 arranged in the third flow passage 69 by the airflow. The airflow generation apparatus 79 may be disposed in the inlet 73 of the first flow passage 65 instead.

Since the sensor apparatus 1 of the fifth embodiment has the above-described configuration, the sensor apparatus 1 of the fifth embodiment can effectively introduce the gas sample 49 onto the sensor elements 3a, 3b and 3c arranged on the base 5. Therefore, even when the concentration of the gas sample 49 introduced into the sensor apparatus 1 is low, the sensor elements 3a, 3b and 3c can still perform detection. Consequently, the target substance 51 can be detected with high accuracy.

Since the sensor apparatus of the fifth embodiment produces the same function and effect as the sensor apparatus of the second embodiment and has the above-described configuration, the sensor apparatus of the fifth embodiment can detect the target substance with higher accuracy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A sensor apparatus comprising:
   a sensor element;

a cover member disposed above the sensor element, which defines a first flow passage, a second flow passage and a third flow passage, wherein the first flow passage takes in a gas sample, the second flow passage introduces the gas sample onto the sensor element, the third flow passage sends the gas sample to an outside of the sensor apparatus, and the first flow passage, the second flow passage and the third flow passage communicate with one another;

an apparatus for maintaining a liquid membrane on the sensor element, comprising:

a liquid supply unit configured to supply a liquid onto the sensor element and to form a liquid membrane, and a liquid discharge unit configured to discharge the liquid in the liquid membrane, wherein the liquid supply unit includes a first container which accommodates the liquid, and the liquid discharge unit includes a space in which the liquid discharged from the liquid membrane is collected and a first member having one end arranged in the space and another end arranged on the sensor element, wherein the liquid discharge unit is configured to discharge the liquid in the liquid membrane by the first member and the first member is made from a non-woven fabric; and an airflow generation apparatus which generates a flow of air flowing from the first flow passage, passing through the second flow passage, and flowing to the third flow passage;

wherein the sensor element is arranged between the liquid supply unit and the liquid discharge unit, and part of the first member of the liquid discharge unit is arranged in the third flow passage.

2. The sensor apparatus of claim 1, wherein the liquid supply unit further includes a capillary whose one end is in contact with the liquid accommodated in the first container and another end is arranged on the sensor element, and the liquid supply unit supplies the liquid onto the sensor element using capillary phenomenon by the capillary.

3. The sensor apparatus of claim 1, wherein the first member is arranged on a line which connects the liquid supply unit and the sensor element.

4. The sensor apparatus of claim 1, wherein the liquid supply unit further includes a pump which adjusts a supply flow rate of the liquid onto the sensor element.

5. The sensor apparatus of claim 4 wherein, wherein the pump is set to a supply flow rate which is lower than a discharge rate of the liquid in the liquid membrane of the liquid discharge unit.

6. The sensor apparatus of claim 1, wherein the liquid supply unit further includes a flow control unit configured to control a flow of the liquid in the liquid membrane, and the flow control unit includes a space in which the liquid is supplied from the liquid supply unit and flows toward the liquid discharge unit.

7. The sensor apparatus of claim 6, wherein the flow control unit suppresses spreading of the liquid supplied from the liquid supply unit.

8. The sensor apparatus of claim 6, wherein the flow control unit includes a liquid retention member which retains the liquid supplied from the liquid supply unit.

9. The sensor apparatus of claim 8, wherein the liquid retention member is arranged on a line which connects the liquid discharge unit and the sensor element.

10. The sensor apparatus of claim 1, wherein the first member of the liquid discharge unit includes a protrusion portion which protrudes toward the liquid supply unit.

11. The sensor apparatus of claim 1, wherein a liquid retention layer which retains the liquid in the liquid membrane is disposed on the sensor element.

12. The sensor apparatus of claim 1, wherein the sensor element includes a sensitive membrane and a biological substance connected to the sensitive membrane, the liquid supply unit forms the liquid membrane on the sensitive membrane of the sensor element, and the biological substance binds to a target substance in a gas sample.

13. The sensor apparatus of claim 12, wherein the sensitive membrane is a graphene membrane, and the graphene membrane is connected to the biological substance by $\pi$-$\pi$ interactions.

14. The sensor apparatus of claim 1, wherein the sensor element is any one of a graphene FET, a carbon nanotube FET, ion sensitivity FET, a surface plasmon resonance element and a surface acoustic wave element.

15. The sensor apparatus of claim 1, wherein the sensor apparatus further comprises a base on which the sensor element is positioned, and an end portion of the first member on the sensor element side is contacted with a surface on the sensor element side of the base.

* * * * *